(12) United States Patent
Su (10) Patent No.: US 7,202,039 B2
(45) Date of Patent: Apr. 10, 2007

(54) COMPLEXITY MANAGEMENT OF GENOMIC DNA

(75) Inventor: Xing Su, Cupertino, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 10/981,222

(22) Filed: Nov. 3, 2004

(65) Prior Publication Data

US 2005/0079536 A1 Apr. 14, 2005

Related U.S. Application Data

(60) Division of application No. 10/013,598, filed on Dec. 10, 2001, now Pat. No. 6,872,529, which is a continuation-in-part of application No. 09/916,135, filed on Jul. 25, 2001, now abandoned.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/23.1

(58) Field of Classification Search .................. None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 5,093,245 A | 3/1992 | Keith et al. | |
| 5,366,877 A | 11/1994 | Keith | |
| 5,409,818 A | 4/1995 | Davey et al. | |
| 5,426,142 A | 6/1995 | Rosano et al. | |
| 5,436,142 A | 7/1995 | Wigler et al. | |
| 5,437,990 A | 8/1995 | Burg et al. | |
| 5,487,985 A | 1/1996 | McClelland et al. | |
| 5,501,964 A | 3/1996 | Wigler et al. | |
| 5,508,178 A | 4/1996 | Rose et al. | |
| 5,565,340 A | 10/1996 | Chenchik et al. | |
| 5,604,097 A | 2/1997 | Brenner | |
| 5,624,825 A | 4/1997 | Walker et al. | |
| 5,691,136 A | 11/1997 | Lupski et al. | |
| 5,702,894 A | 12/1997 | Modrich et al. | |
| 5,712,127 A | 1/1998 | Malek et al. | |
| 5,716,785 A | 2/1998 | Van Gelder et al. | |
| 5,759,822 A | 6/1998 | Chenchik et al. | |
| 5,763,239 A | 6/1998 | Short et al. | |
| 5,858,656 A | 1/1999 | Deugau et al. | |
| 5,874,215 A | 2/1999 | Kuiper et al. | |
| 5,876,929 A | 3/1999 | Wigler et al. | |
| 5,972,693 A | 10/1999 | Rothberg et al. | |
| 6,001,574 A | 12/1999 | Short et al. | |
| 6,004,783 A | 12/1999 | Ausubel et al. | |
| 6,045,994 A | 4/2000 | Zabeau et al. | |
| 6,060,245 A | 5/2000 | Sorge et al. | |
| 6,100,030 A | 8/2000 | McCasky et al. | |
| 6,107,023 A | 8/2000 | Reyes et al. | |
| 6,110,711 A | 8/2000 | Serafini et al. | |
| 6,114,149 A * | 9/2000 | Fry et al. ................. 435/91.2 |
| 6,114,152 A | 9/2000 | Serafini et al. | |
| 6,124,090 A | 9/2000 | Rose et al. | |
| 6,174,670 B1 * | 1/2001 | Wittwer et al. ............. 435/6 |
| 6,197,557 B1 | 3/2001 | Makarov et al. | |
| 6,207,372 B1 | 3/2001 | Shuber | |
| 6,207,379 B1 | 3/2001 | Lee et al. | |
| 6,218,119 B1 | 4/2001 | Kuiper et al. | |
| 6,232,067 B1 | 5/2001 | Hunkapiller et al. | |
| 6,268,133 B1 | 7/2001 | Nisson et al. | |
| 6,277,606 B1 | 8/2001 | Wigler et al. | |
| 6,287,825 B1 | 9/2001 | Weissman et al. | |
| 6,472,185 B2 | 10/2002 | McCasky et al. | |
| 2002/0119448 A1 | 8/2002 | Sorge et al. | |
| 2003/0032020 A1* | 2/2003 | Brenner ...................... 435/6 |

FOREIGN PATENT DOCUMENTS

| | | |
|---|---|---|
| EP | 0224126 A2 | 6/1987 |
| WO | WO90/08821 | 8/1990 |
| WO | WO91/05861 | 5/1991 |
| WO | WO00/18960 | 4/2000 |
| WO | WO01/75163 A2 | 10/2001 |
| WO | WO02/20844 A1 | 3/2002 |

OTHER PUBLICATIONS

Mitsunaga et al. (1998) A nested PCR-RFLP method for high-resolution typing of HLA-A alleles. European Journal of Immunogenetics. vol. 25, pp. 15-27.*

Bernd W. Kalisch, et al., Gene: "An International Journal of Focusing on Gene Cloning and Gene Structure and Function", Department of Medical Biochemistry, Faculty of Medicine, University of Calgary, Calgary, ALberta T2N 4N1 (Canada), pp. 263-270.

Dmitry A. Shagin, et al., "Regulation of Average Length of Complex PCR Product", Nucleic Acids Research, 1999, vol. 27, No. 18, © 1999 Oxford University Press, Institute of Bioorganic Chemistry Miklukho-Maklaya 16/10, 117871 Moscow, Russia, Received Jun. 8, 1999; Revised and Accepted Jul. 23, 1999, 3 pp.

(Continued)

*Primary Examiner*—Jeffrey Fredman
*Assistant Examiner*—Angela Bertagna
(74) *Attorney, Agent, or Firm*—Sandra E. Wells (57) ABSTRACT

The presently claimed invention provides for novel methods and kits for reducing the complexity of a nucleic acid sample by providing non-gel based methods for size fractionation. In a preferred embodiment, size fractionation can be accomplished by varying conditions or reagents of a PCR reaction to amplify fragments of specific size ranges. The invention further provides for analysis of the above sample by hybridization to an array, which may be specifically designed to interrogate the desired fragments for particular characteristics, such as, for example, the presence or absence of a polymorphism.

15 Claims, 2 Drawing Sheets

OTHER PUBLICATIONS

"Introducing Eclipse™ Probes," Synthetic Genetics, 3347 Industrial Ct., Sand Diego, CA, 92121, 6 pp, http:/www.syntheticgenetics.com/eclipse/index.html.

K. A. Lukyanov, et al., "Inverted Terminal Repeats Permit the Average Length of Amplified DNA Fragments to be Regulated During Preparation of cDNA Libraries by Polymerase Chain reaction", Analytical Biochemistry 198-202 (1995), Copyright © 1995 by Academic Press, Inc.

Kenneth H. Roux et al, "A Strategy for Single Site PCR Amplification of dsDNA: Priming Digested Cloned on Genomic DNA from an Anchor-Modified Restriction Site and a Short Internal Sequence", BioTechniques, vol. 8, No. 1 (1990), 7 pp.

Konstantine Lukyanov, et al., "Construction of cDNA Libraries from Small Amounts of Total RNA Using the Suppression PCR Effect", Biochemical and Biophysical Research Communications 285-288 (1997), Article No. RC965948, Received Dec. 6, 1996, Copyright © 1997 by Academic Press.

Nikolai Lisitsyn, et al., Research Article "Cloning the Differences Between Two Complex Genomes", Science, vol. 259, Feb. 12, 1993, pp. 946-951.

* cited by examiner

COMPLEXITY MANAGEMENT OF GENOMIC DNA

RELATED APPLICATIONS

The present application is a divisional of U.S. patent application Ser. No. 10/013,598 filed on Dec. 10, 2001, now U.S. Pat. No. 6,872,529 which is a continuation-in-part of U.S. application Ser. No. 09/916,135 filed Jul. 25, 2001, now abandoned which is incorporated herein in its entirety by reference.

FIELD OF THE INVENTION

The invention relates to enrichment and amplification of sequences from a nucleic acid sample. In one embodiment, the invention relates to enrichment and amplification of nucleic acids for the purpose of further analysis. The present invention relates to the fields of molecular biology and genetics.

BACKGROUND OF THE INVENTION

The past years have seen a dynamic change in the ability of science to comprehend vast amounts of data. Pioneering technologies such as nucleic acid arrays allow scientists to delve into the world of genetics in far greater detail than ever before. Exploration of genomic DNA has long been a dream of the scientific community. Held within the complex structures of genomic DNA lies the potential to identify, diagnose, or treat diseases like cancer, Alzheimer disease or alcoholism. Exploitation of genomic information from plants and animals may also provide answers to the world's food distribution problems.

Recent efforts in the scientific community, such as the publication of the draft sequence of the human genome in February 2001, have changed the dream of genome exploration into a reality. Genome-wide assays, however, must contend with the complexity of genomes; the human genome for example is estimated to have a complexity of $3 \times 10^9$ base pairs. Novel methods of sample preparation and sample analysis that reduce complexity may provide for the fast and cost effective exploration of complex samples of nucleic acids, particularly genomic DNA.

SUMMARY OF THE INVENTION

The present invention provides for novel methods of sample preparation and analysis comprising managing or reducing the complexity of a nucleic acid sample. The methods of the invention generally involve fragmenting a sample and digesting the fragments with an exonuclease to produce single-stranded half molecules, which are then amplified. The invention further controls the average length of product in an amplification reaction by varying the conditions and or components of the reaction so that size selection and target amplification are achieved in a single step. Splitting the relatively large fragments into half molecules facilitates amplification of these fragments in small molecule form, allowing maintenance of the sequence information in large fragments under conditions that, without splitting, would not be amplified. The methods are preferably non-gel based. The invention further provides for analysis of the sample by hybridization to an array, which may be specifically designed to interrogate fragments for particular characteristics, such as, for example, the presence or absence of a polymorphism. The invention further provides for methods of designing an array to interrogate particular subsets of fragments. In a preferred embodiment the invention discloses novel methods of genome-wide polymorphism discovery and genotyping.

In one embodiment the step of complexity management of the nucleic acid comprises fragmenting the nucleic acid sample to form fragments, ligating adaptor sequences to the fragments, digesting the fragments to form single-stranded half molecules, making the half molecules double-stranded and amplifying the fragments under conditions that favor amplification of a particular size range of fragments.

PCR conditions that may be varied include: the extension time, the annealing time, concentration of primer, primer length, presence or absence of a 3' to 5' exonuclease activity and concentration of nucleotide analogs. Another step that can be used to control average length of the amplification product is the introduction of regions of complementarity in the 5' and 3' ends of the target fragments. One way to accomplish this is through ligation of a single adaptor sequence to both ends of the fragments. In general the methods use a single round of amplification, but in some embodiments the first amplification product is diluted and amplified with a second round of amplification which is preferably done under conditions that favor amplification of a particular size range of fragments.

In one embodiment the PCR conditions are optimized to amplify fragments that are approximately the length of the fragments to be amplified.

In one embodiment, the invention relates to a kit comprising reagents and instructions for amplifying a subset of fragments. The kit may comprise reagents and instructions necessary for amplification of one or more subsets of fragments.

DETAILED DESCRIPTION OF THE PREFERRED EMBODIMENTS (A) General

The present invention provides a flexible and scalable method for analyzing complex samples of nucleic acids, such as genomic DNA. These methods are not limited to any particular type of nucleic acid sample: plant, bacterial, animal (including human) total genome DNA, RNA, cDNA and the like may be analyzed using some or all of the methods disclosed in this invention. The word "DNA" may be used below as an example of a nucleic acid. It is understood that this term includes all nucleic acids, such as DNA and RNA, unless a use below requires a specific type of nucleic acid. This invention provides a powerful tool for analysis of complex nucleic acid samples. From experimental design to isolation of desired fragments and hybridization to an appropriate array, the invention provides for fast, efficient and inexpensive methods of complex nucleic acid analysis.

The present invention relies on many patents, applications and other references for details known to those of the art. Therefore, when a patent, application, or other reference is cited or repeated below, it should be understood that it is incorporated by reference in its entirety for all purposes as well as for the proposition that is recited. As used in the specification and claims, the singular form "a," "an," and "the" include plural references unless the context clearly dictates otherwise. For example, the term "an agent" includes a plurality of agents, including mixtures thereof. An individual is not limited to a human being but may also be other organisms including but not limited to mammals, plants, bacteria, or cells derived from any of the above.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as common individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. The same holds true for ranges in increments of $10^5$, $10^4$, $10^3$, $10^2$, 10, $10^{-1}$, $10^{-2}$, $10^{-3}$, $10^{-4}$, or $10^{-5}$, for example. This applies regardless of the breadth of the range.

The practice of the present invention may employ, unless otherwise indicated, conventional techniques of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example hereinbelow. However, other equivalent conventional procedures can, of course, also be used. Such conventional techniques can be found in standard laboratory manuals such as *Genome Analysis: A Laboratory Manual Series (Vols. I–IV)*, *Using Antibodies: A Laboratory Manual*, *Cells: A Laboratory Manual*, *PCR Primer: A Laboratory Manual*, and *Molecular Cloning: A Laboratory Manual* (all from Cold Spring Harbor Laboratory Press), all of which are herein incorporated in their entirety by reference for all purposes.

Some aspects of the present invention make use of microarrays, also called arrays. Methods and techniques applicable to array synthesis have been described in U.S. Pat. Nos. 5,143,854, 5,242,974, 5,252,743, 5,324,633, 5,384,261, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, and 6,090,555. All of the above patents incorporated herein by reference in their entireties for all purposes.

The word "DNA" may be used below as an example of a nucleic acid. It is understood that this term includes all nucleic acids, such as DNA and RNA, unless a use below requires a specific type of nucleic acid.

(B) Definitions

Nucleic acids according to the present invention may include any polymer or oligomer of pyrimidine and purine bases, preferably cytosine, thymine, and uracil, and adenine and guanine, respectively. (See Albert L. Lehninger, *Principles of Biochemistry*, at 793–800 (Worth Pub. 1982) which is herein incorporated in its entirety for all purposes).

Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 20 nucleotides in length, but may be up to 50, 100, 1000, or 5000 nucleotides long or a compound that specifically hybridizes to a polynucleotide. Polynucleotides of the present invention include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "fragment," "segment," or "DNA segment" refers to a portion of a larger DNA polynucleotide or DNA. A polynucleotide, for example, can be broken up, or fragmented into, a plurality of segments. Various methods of fragmenting nucleic acid are well known in the art. These methods may be, for example, either chemical or physical in nature. Chemical fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave DNA at known or unknown locations. Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale. Other physical methods include sonication and nebulization. Combinations of physical and chemical fragmentation methods may likewise be employed such as fragmentation by heat and ion-mediated hydrolysis. See for example, Sambrook et al., "Molecular Cloning: A Laboratory Manual," $3^{rd}$ Ed. Cold Spring Harbor Laboratory Press, Cold Spring Harbor, N.Y. (2001) ("Sambrook et al.) which is incorporated herein by reference for all purposes. These methods can be optimized to digest a nucleic acid into fragments of a selected size range. Useful size ranges may be from 100, 200, 400, 700 or 1000 to 500, 800, 1500, 2000, 4000 or 10,000 base pairs. However, larger size ranges such as 4000, 10,000 or 20,000 to 10,000, 20,000 or 500,000 base pairs may also be useful.

A number of methods disclosed herein require the use of restriction enzymes to fragment the nucleic acid sample. In general, a restriction enzyme recognizes a specific nucleotide sequence of four to eight nucleotides and cuts the DNA at a site within or a specific distance from the recognition sequence. For example, the restriction enzyme EcoRI recognizes the sequence GAATTC and will cut a DNA molecule between the G and the first A. The length of the recognition sequence is inversely proportional to the frequency of occurrence of the site in the genome. A simplistic theoretical estimate is that a six base-pair recognition sequence will occur once in every 4096 ($4^6$) base pairs while a four base-pair recognition sequence will occur once every 256 ($4^4$) base pairs. In silico digestions of sequences from the Human Genome Project show that the actual occurrences are even more infrequent, depending on the sequence of the restriction site. Because the restriction sites are rare, the appearance of shorter restriction fragments, for example those less than 1000 base pairs, is much less frequent than the appearance of longer fragments. Many different restriction enzymes are known and appropriate restriction enzymes can be selected for a desired result. (For a description of many restriction enzymes see, New England BioLabs Catalog, which is herein incorporated by reference in its entirety for all purposes).

"Adaptor sequences" or "adaptors" are generally oligonucleotides of at least 5, 10, or 15 bases and preferably no more than 50 or 60 bases in length, however, they may be even longer, up to 100 or 200 bases. Adaptor sequences may be synthesized using any methods known to those of skill in the art. For the purposes of this invention they may, as options, comprise primer binding sites, restriction sites and promoters. The adaptor may be entirely or substantially double-stranded. The adaptor may be phosphorylated or unphosphorylated on one or both strands. Adaptors are particularly useful in one embodiment of the current invention if they comprise a substantially double-stranded region and short single-stranded regions which are complementary to the single-stranded region created by digestion with a restriction enzyme. For example, when DNA is digested with the restriction enzyme EcoRI the resulting double-stranded fragments are flanked at either end by the single-stranded overhang 5'-AATT-3', an adaptor that carries a single-stranded overhang 5'-AATT-3' will hybridize to the fragment through complementarity between the overhanging regions. This "sticky end" hybridization of the adaptor to the fragment may facilitate ligation of the adaptor to the fragment but blunt ended ligation is also possible. Blunt ends can be converted to sticky ends using the exonuclease activity of the Klenow fragment. For example when DNA is digested with PvuII the blunt ends can be converted to a two base pair overhang by incubating the fragments with Klenow in the presence of dTTP and dCTP.

Adaptors can be used to introduce complementarity between the ends of a nucleic acid. For example, if a double stranded region of DNA is digested with a single enzyme so that each of the ends of the resulting fragments is generated by digestion with the same restriction enzyme, both ends will have the same overhanging sequence. For example if a nucleic acid sample is digested with EcoRI both strands of the DNA will have at their 5' ends a single stranded region, or overhang, of 5'-AATT-3'. A single adaptor that has a complementary overhang of 5'-AATT-3' can be ligated to both ends of the fragment. Each of the strands of the fragment will have one strand of the adaptor ligated to the 5' end and the second strand of the adaptor ligated to the 3' end. The two strands of the adaptor are complementary to one another so the resulting ends of the individual strands of the fragment will be complementary.

A single adaptor can also be ligated to both ends of a fragment resulting from digestion with two different enzymes. For example, if the method of digestion generates blunt ended fragments, the same adaptor sequence can be ligated to both ends. Alternatively some pairs of enzymes leave identical overhanging sequences. For example, BglII recognizes the sequence 5'-AGATCT-3', cutting after the first A, and BamHI recognizes the sequence 5'-GGATCC-3', cutting after the first G; both leave an overhang of 5'-GATC-3'. A single adaptor with an overhang of 5'-GATC-3' may be ligated to both digestion products.

Digestion with two or more enzymes can be used to selectively ligate separate adaptors to either end of a restriction fragment. For example, if a fragment is the result of digestion with EcoRI at one end and BamHI at the other end, the overhangs will be 5'-AATT-3' and 5'GATC-3', respectively. An adaptor with an overhang of AATT will be preferentially ligated to one end while an adaptor with an overhang of GATC will be preferentially ligated to the second end.

"Genome" designates or denotes the complete, single-copy set of genetic instructions for an organism as coded into the DNA of the organism. A genome may be multi-chromosomal such that the DNA is cellularly distributed among a plurality of individual chromosomes. For example, in human there are 22 pairs of chromosomes plus a gender associated XX or XY pair.

The term "chromosome" refers to the heredity-bearing gene carrier of a living cell which is derived from chromatin and which comprises DNA and protein components (especially histones). The conventional internationally recognized individual human genome chromosome numbering system is employed herein. The size of an individual chromosome can vary from one type to another with a given multi-chromosomal genome and from one genome to another. In the case of the human genome, the entire DNA mass of a given chromosome is usually greater than about 100,000,000 bp. For example, the size of the entire human genome is about $3 \times 10^9$ bp. The largest chromosome, chromosome no. 1, contains about $2.4 \times 10^8$ bp while the smallest chromosome, chromosome no. 22, contains about $5.3 \times 10^7$ bp.

A "chromosomal region" is a portion of a chromosome. The actual physical size or extent of any individual chromosomal region can vary greatly. The term "region" is not necessarily definitive of a particular one or more genes because a region need not take into specific account the particular coding segments (exons) of an individual gene.

The term genotyping refers to the determination of the genetic information an individual carries at one or more positions in the genome. For example, genotyping may comprise the determination of which allele or alleles an individual carries for a single SNP or the determination of which allele or alleles an individual carries for a plurality of SNPs.

The term "target sequence", "target nucleic acid" or "target" refers to a nucleic acid of interest. The target sequence may or may not be of biological significance. Typically, though not always, it is the significance of the target sequence which is being studied in a particular experiment. As non-limiting examples, target sequences may include regions of genomic DNA which are believed to contain one or more polymorphic sites, DNA encoding or believed to encode genes or portions of genes of known or unknown function, DNA encoding or believed to encode proteins or portions of proteins of known or unknown function, DNA encoding or believed to encode regulatory regions such as promoter sequences, splicing signals, polyadenylation signals, etc. The number of sequences to be interrogated can vary, but preferably are from 1, 10, 100, 1000, or 10,000, 100,000 or 1,000,000 target sequences.

The term subset or representative subset refers to a fraction of a genome. The subset may be 0.1, 1, 3, 5, 10, 25, 50 or 75% of the genome. The partitioning of fragments into subsets may be done according to a variety of physical characteristics of individual fragments. For example, fragments may be divided into subsets according to size, according to the particular combination of restriction sites at the ends of the fragment, or based on the presence or absence of one or more particular sequences.

An "array" comprises a support, preferably solid, with nucleic acid probes attached to the support. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186 and Fodor et al., *Science,* 251:767–777 (1991). Each of which is incorporated by reference in its entirety for all purposes.

Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789,162, 5,708,153, 6,040,193 and 5,800,992, which are hereby incorporated by reference in their entirety for all purposes.)

Arrays may be packaged in such a manner as to allow for diagnostic use or can be an all-inclusive device; e.g., U.S. Pat. Nos. 5,856,174 and 5,922,591 incorporated in their entirety by reference for all purposes.

Preferred arrays are commercially available from Affymetrix under the brand name GeneChip® and are directed to a variety of purposes, including genotyping and gene expression monitoring for a variety of eukaryotic and prokaryotic species. (See Affymetrix Inc., Santa Clara and their website at affymetrix.com.)

Hybridization probes are oligonucleotides capable of binding in a base-specific manner to a complementary strand of nucleic acid. Such probes include peptide nucleic acids, as described in Nielsen et al., *Science* 254, 1497–1500 (1991), and other nucleic acid analogs and nucleic acid mimetics. See U.S. patent application Ser. No. 08/630,427-filed Apr. 3, 1996.

Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25–30° C. are suitable for allele-specific probe hybridizations. For stringent conditions, see, for example, Sambrook, Fritsche and Maniatis. "Molecular Cloning A laboratory Manual" $2^{nd}$ Ed. Cold Spring Harbor Press (1989) which is hereby incorporated by reference in its entirety for all purposes above.

Polymorphism refers to the occurrence of two or more genetically determined alternative sequences or alleles in a population. A polymorphic marker or site is the locus at which divergence occurs. Preferred markers have at least two alleles, each occurring at frequency of preferably greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens.

Single nucleotide polymorphisms (SNPs) are positions at which two alternative bases occur at appreciable frequency (>1%) in the human population, and are the most common type of human genetic variation. The site is usually preceded by and followed by highly conserved sequences of the allele (e.g., sequences that vary in less than $\frac{1}{100}$ or $\frac{1}{1000}$ members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

An individual is not limited to a human being, but may also include other organisms including but not limited to mammals, plants, bacteria or cells derived from any of the above.

In silico digestion is a computer aided simulation of enzymatic digests accomplished by searching a sequence for restriction sites. In silico digestion provides for the use of a computer system to model enzymatic reactions in order to determine experimental conditions before conducting any actual experiments. An example of an experiment would be to model digestion of the human genome with specific restriction enzymes to predict the sizes of the resulting restriction fragments.

The Noise Likelihood Factor (NLF) is a measure of the likelihood that a SNP is "present" in the subset of genome that was hybridized to the array. A decreasing NLF score is an indication of increased confidence that the SNP is present in the sample. A score of −6 was used as the cut off for determining significance. The NLF cutoff can be set at a more stringent level of −10 or −15.

Splitting is the process of digesting a double-stranded fragment with an exonuclease to produce two single-stranded half molecules. The splitting is typically followed by a step that generates double-stranded half molecules. Splitting can be used to divide a large fragment into two smaller fragments. The fragments may be of approximately equal size.

(C.) Complexity Management

The present invention provides for novel methods of sample preparation and analysis involving managing or reducing the complexity of a nucleic acid sample, such as genomic DNA, by amplifying a representative subset of the sample. The invention further provides for analysis of the above subset by hybridization to an array which may be specifically designed to interrogate the desired fragments for particular characteristics, such as, for example, the presence or absence of a polymorphism. The invention is particularly useful when combined with other methods of genome analysis. As an example, the present techniques are useful to genotype individuals after polymorphisms have been identified.

One method that has been used to isolate a subset of a genome is to separate fragments according to size by electrophoresis in a gel matrix. The region of the gel containing fragments in the desired size range is then excised and the fragments are purified away from the gel matrix. The SNP consortium (TSC) adopted this approach in their efforts to discover single nucleotide polymorphisms (SNPs) in the human genome. See, Altshuler et al., *Science* 407: 513–516 (2000) and The International SNP Map Working Group, *Nature* 409: 928–933 (2001) both of which are herein incorporated by reference in their entirety for all purposes.

The present invention provides methods of complexity management of nucleic acid samples, such as genomic DNA, that can be used as an alternative to separation of fragments by gel electrophoresis and purification of fragments from a gel matrix. Generally, the embodiments include the steps of: fragmenting the nucleic acid by digestion with one or more restriction enzymes or through alternative methods of fragmentation; ligating adaptors to the ends of the fragments; digesting the fragments to produce single stranded half molecules, making the single stranded half molecules double stranded and amplifying a subset of the fragments using amplification conditions that selectively amplify fragments of a desired size range. In a preferred embodiment the amplified sequences are then exposed to an array which may or may not have been specifically designed and manufactured to interrogate the isolated sequences. Design of both the complexity management steps and the arrays may be aided by computer modeling techniques. Generally, the steps of the present invention involve reducing the complexity of a nucleic acid sample using the disclosed techniques alone or in combination. None of these techniques requires purification of the fragments from a gel matrix.

When interrogating genomes it is often useful to first reduce the complexity of the sample and analyze one or more subsets of the genome. Subsets can be defined by many characteristics of the fragments. In a preferred embodiment of the current invention, the subsets are defined by the size of the fragments. Useful size ranges may be from 100, 200, 400, 700, 1000 or 2000 to 500, 800, 1500, 2000, 3000, 4000 or 10,000. However, larger size ranges such as 4000, 10,000 or 20,000 to 10,000, 20,000 or 500,000 base pairs may also be useful.

It will be understood by those of skilled in the art that a subset will be composed primarily of fragments from the selected size range, but some fragments that are longer or shorter than the selected size range may also be present in the amplification product.

The genomic DNA sample of the current invention may be isolated according to methods known in the art, such as PCR, reverse transcription, and the like. It may be obtained from any biological or environmental source, including plant, animal (including human), bacteria, fungi or algae. Any suitable biological sample can be used for assay of genomic DNA. Convenient suitable samples include whole blood, tissue, semen, saliva, tears, urine, fecal material, sweat, buccal, skin and hair.

Fragmentation of the sample may be done by any known method. In a preferred embodiment of the current invention the sample nucleic acid is fragmented using one or more restriction enzymes.

In a preferred embodiment of the current invention adaptors are ligated to the ends of the fragments. In one embodiment a single adaptor is ligated to both ends of the fragments. In one embodiment the adaptor introduces complementarity between the fragment ends. In many of the embodiments of the current invention the adaptors comprise primer binding sites. In another preferred embodiment the adaptors are ligated to the fragments after double-stranded half molecules are generated.

Methods of ligation will be known to those of skill in the art and are described, for example in Sambrook et at. and the New England BioLabs catalog both of which are incorporated herein by reference for all purposes. Methods include using T4 DNA Ligase which catalyzes the formation of a phosphodiester bond between juxtaposed 5' phosphate and 3' hydroxyl termini in duplex DNA or RNA with blunt or and sticky ends; Taq DNA ligase which catalyzes the formation of a phosphodiester bond between juxtaposed 5' phosphate and 3' hydroxyl termini of two adjacent oligonucleotides which are hybridized to a complementary target DNA; *E. coli* DNA ligase which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3'–>5' phosphodiester bond, substrates include single-stranded RNA and DNA as well as dinucleoside pyrophosphates; or any other methods described in the art.

In the current invention, prior to PCR amplification the fragments are split into two molecules of approximately equal size. This allows sequences of larger molecules to be amplified under conditions that are optimized to amplify smaller fragments. The current invention is particularly useful when combined with the previously described methods of U.S. patent application Ser. No. 09/916,135, which is herein incorporated by reference in its entirety for all purposes. The Ser. No. 09/916,135 application describes methods for modulating the size of amplified fragments in an amplification reaction by varying the conditions of the reaction so that fragments of a certain size are preferentially amplified. The current invention adds an additional step to these methods, which allows for amplification of a second set of fragments using a single set of amplification conditions. For example, if a given set of PCR conditions favors amplification of fragments that are 400–800 base pairs long, the current invention allows sequences for fragments of 800–1600 base pairs to be amplified under the same conditions. This is accomplished by splitting fragments into two approximately equal size fragments. For example a fragment that is 1600 base pairs can be split into 2 fragments of approximately 800 base pairs prior to amplification.

Figure 1:
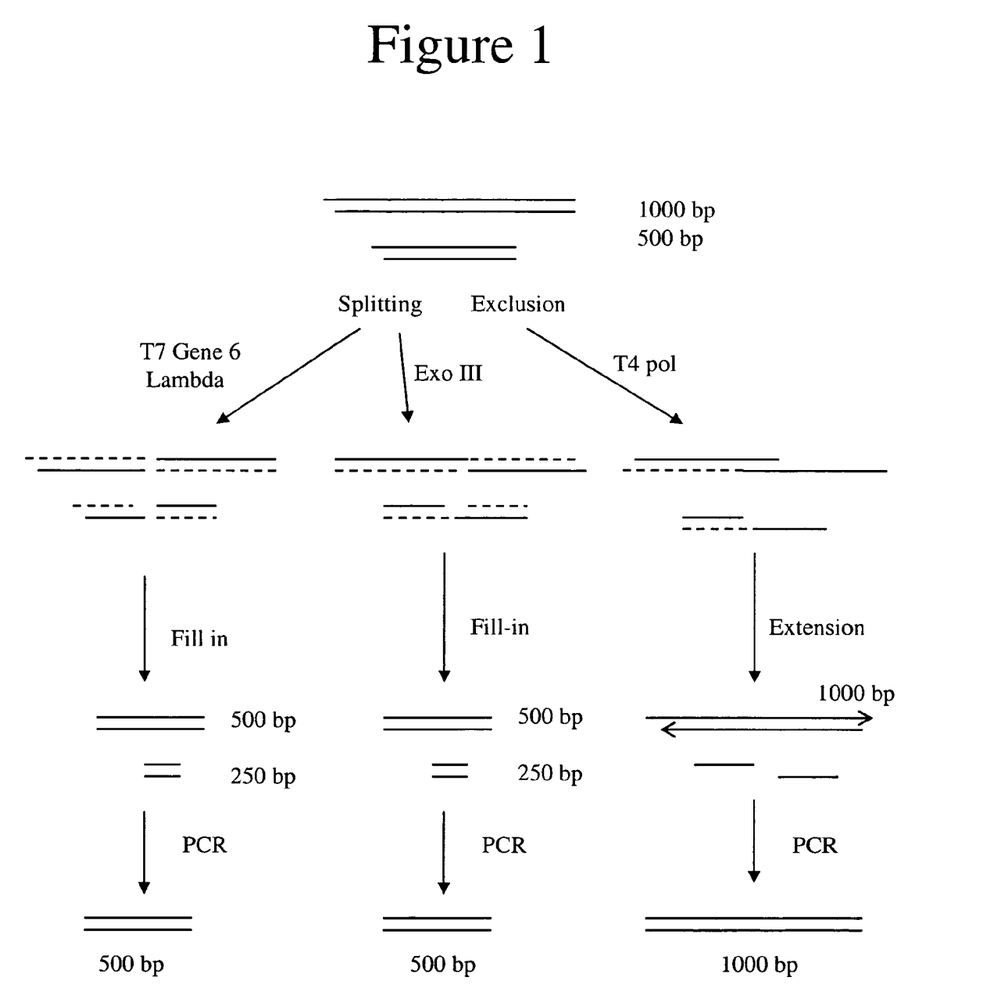
FIG. 1 shows a schematic of size selection using different exonucleases to digest restriction fragments followed by PCR under conditions that amplify a selected size range of fragments.

Splitting may be accomplished by any method known in the art. In a preferred embodiment of the invention fragments are digested with a nuclease that digests one strand of a double stranded fragment. Preferably the enzyme is specific for double stranded fragments and will digest in only one direction, 5' to 3' or 3' to 5'. In a preferred embodiment the enzyme requires a double stranded template and digestion stops when enzymes digesting opposite strands meet, preferably at approximately the middle of the fragment, see FIG. 1.

Enzymes that may be used include, for example, exonuclease III, T7 exonuclease also known as T7 Gene 6 protein and Lambda exonuclease. (USB, Cleveland, Ohio) Exonuclease III is a 3' to 5' exonuclease that catalyzes the stepwise removal of mononucleotides from 3'-hydroxyl temini of duplex DNA. The preferred substrates are blunt or recessed 3'-termini. The enzyme is not active on single-stranded DNA, and thus 3'-protruding termini are resistant to cleavage. The degree of resistance depends on the length of the extension, with extensions 4 bases or longer being essentially resistant to cleavage. This property can be exploited to produce unidirectional deletions from a linear molecule with one resistant (3'-overhang) and one susceptible (blunt or 5'-overhang) terminus.

T7 exonuclease (NEB) and T7 Gene 6 exonuclease (AP Biotech, USB) act in the 5' to 3'direction, catalyzing the removal of 5' mononucleotides from duplex DNA. T7 Exonuclease is able to initiate nucleotide removal from the 5'termini or at gaps and nicks of double-stranded DNA. It will degrade both 5'phosphorylated or 5' dephosphorylated DNA. It has been also reported to degrade RNA and DNA from RNA/DNA hybrids in the 5' to 3' direction.

Lambda exonuclease is a highly processive enzyme that acts in the 5' to 3' direction, catalyzing the removal of 5' mononucleotides from duplex DNA. The preferred substrate is 5'-phosphorylated doublestranded DNA, although it will also degrade single-stranded and non-phosphorylated substrates at a greatly reduced rate.

Other enzymes such as T4 DNA Polymerase (NEB) can also be used. T4 DNA Polymerase catalyzes the synthesis of DNA in the 5' to 3' direction but also has a 3' to 5' exonuclease activity.

These enzymes are available from a variety of sources including New England Biolabs and APBiotech. (See, the NEB, AP Biotech and USB catalogues available on the internet at apbiotech.com and, neb.com last visited Aug. 16, 2001, which are both incorporated herein by reference for all purposes). Any enzyme that digests nucleic acid in a single direction and is specific for double-stranded nucleic acids could be used.

The reaction conditions of the exonuclease digestion may be modulated by, for example, the inclusion of DMSO or single-strand DNA binding proteins such as SSB or T4 Gene 32 protein (NEB, USB), or by varying the temperature (16° C.–52° C.) and/or the concentration of Mg++ (1–5 mM).

Following splitting, the single-stranded half molecules are preferably converted to double-stranded fragments. In one embodiment, illustrated in FIG. 2, Terminal Transferase (TdT, available from Promega) is used to add nucleotides to the end of the half molecules. TdT is a template independent polymerase that catalyzes the addition of deoxynucleotides to the 3' hydroxyl terminus of DNA molecules. The enzyme can be used to add, for example, a homopolymer tail of A's to the end of the half molecules. A primer comprised of a 3' stretch of oligo (dT) linked to a 5' sequence can then be annealed to the oligo (dA) which can be extended to form double-stranded fragments using the primer as a template. The 5' sequence may comprise a primer binding site or a polymerase promoter such as a T7 promoter. The fragments can then be amplified by, for example, PCR using one or more primers designed to hybridize to the adaptor sequence and the filled-in primer binding site. In a particularly preferred embodiment, a single primer or primer pair can be used for amplification. The adaptor sequences can also be ligated to the fragments after the single-stranded half molecules are converted to double-stranded half molecules.

The complexity of the amplified sample can be further reduced by adding one or more bases to the 3' end of the PCR primer. In this embodiment of the current invention, the primer binding site on the fill-in primer comprises the sequence of the adaptor plus additional bases, a single primer can be used for PCR amplification There are many known methods of amplifying nucleic acid sequences including e.g., PCR. See, e.g., *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (eds. McPherson et al., IRL Press, Oxford); and U.S. Pat. Nos. 4,683,202, 4,683,195, 4,800,159 4,965,188 and 5,333,675 each of which is incorporated herein by reference in their entireties for all purposes.

PCR is an extremely powerful technique for amplifying specific polynucleotide sequences, including genomic DNA, single-stranded cDNA, and MRNA among others. Various methods of conducting PCR amplification and primer design and construction for PCR amplification will be known to those of skill in the art. Generally, in PCR a double-stranded DNA to be amplified is denatured by heating the sample. New DNA synthesis is then primed by hybridizing primers to the target sequence in the presence of DNA polymerase and excess dNTPs. In subsequent cycles, the primers hybridize to the newly synthesized DNA to produce discreet products with the primer sequences at either end. The products accumulate exponentially with each successive round of amplification.

The DNA polymerase used in PCR is often a thermostable polymerase. This allows the enzyme to continue functioning after repeated cycles of heating necessary to denature the double-stranded DNA. Polymerases that are useful for PCR include, for example, Taq DNA polymerase, Tth DNA polymerase, Tfl DNA polymerase, Tma DNA polymerase, Tli DNA polymerase, and Pt DNA polymerase. There are many commercially available modified forms of these enzymes including: AmpliTaq® and AmpliTaq Gold® both available from Applied Biosystems. Many are available with or without a 3- to 5' proofreading exonuclease activity. See, for example, Vent® and Vent® (exo-) available from New England Biolabs.

Other suitable amplification methods include the ligase chain reaction (LCR) (e.g., Wu and Wallace, *Genomics* 4, 560 (1989) and Landegren et al., *Science* 241, 1077 (1988)), transcription amplification (Kwoh et al., *Proc. Natl. Acad. Sci. USA* 86, 1173 (1989)), and self-sustained sequence replication (Guatelli et al., *Proc. Nat. Acad. Sci. USA,* 87, 1874 (1990)) and nucleic acid based sequence amplification (NABSA). (See, U.S. Pat. Nos. 5,409,818, 5,554,517, and 6,063,603). The latter two amplification methods include isothermal reactions based on isothermal transcription, which produce both single-stranded RNA (ssRNA) and double-stranded DNA (dsDNA) as the amplification products in a ratio of about 30 or 100 to 1, respectively.

When genomic DNA is digested with one or more restriction enzymes the sizes of the fragments are randomly distributed over a broad range. Following adaptor ligation, all of the fragments that have adaptors ligated to both ends will compete equally for primer binding and amplification in many methods of amplification, regardless of size. The conditions of an amplification can be biased toward amplification of fragments of a selected size range. For example, short extension times favor amplification of smaller fragments because length of extension is limited by extension time. Longer fragments require longer extension times because shorter extension times can result in termination of the extension product prior to completion. These prematurely terminated products will not serve as templates for subsequent rounds of amplification because they will be lacking the required primer binding site at their 3' end. The average size of the amplification product can also be controlled by varying the length of the adaptor, the sequence of the adaptor and the concentration of primer in the amplification reaction. The size of the amplification product can also be controlled by the addition of varying concentrations of chain terminating nucleotide analogs or an enzyme activity, such as a 3' to 5' exonuclease activity. Because of the geometric nature of PCR amplification, subtle differences in yields that occur in the initial cycles, will result in significant differences in yields in later cycles. (See, PCR Primer: A Laboratory Manual, CSHL Press, Eds. Carl Dieffenbach and Gabriela Dveskler, (1995), (Dieffenbach et al.) which is herein incorporated by reference in its entirety for all purposes.)

In a preferred embodiment the methods of the current invention are combined with amplification conditions that are optimized for a first size range to allow amplification of restriction fragments that are approximately twice the length of the first size range. In this way the current invention allows amplification of a broader size range of fragments using a single set of amplification conditions.

The current invention is particularly useful when combined with PCR conditions that control the average length of the amplification product by ligating adaptors to the fragments that introduce a region of complementarity between the 5' and 3' ends of the fragment. During the primer annealing phase of amplification, self-annealing of the ends of the template will compete with binding of the primer to the template. The probability of self-annealing is proportional to the length of the fragment so the probability that the ends of a shorter fragment will self-anneal is higher than the probability that the ends of a longer fragment will self-anneal. (See, Brownie et al, *Nucleic Acids Research*, 25:3235–3241, (1997), which is herein incorporated by reference in its entirety for all purposes.)

Under these conditions of amplification the length of the amplification product is also dependent on the concentration of added primer. Primer binding is competing with self-annealing so the probability that a primer will bind depends on the concentration of the primer. If, for example, amplification of short fragments is desired, higher primer concentration should be used. In general, higher primer concentrations favor primer binding and amplification of shorter fragments while decreased primer concentration favors amplification of longer fragments. Preferably the range of primer concentration is from 0.1, 0.3, or 0.5 μM, to 0.5, 1, 2 or 10 μM.

The concentration of salt in the reaction, for example, $MgCl_2$ may also be manipulated to favor amplification of a selected size of fragments. It may be necessary to titrate salt concentration for optimization. The denaturation temperature can also be varied to favor amplification of selected fragments. (See, Current Protocols in Molecular Biology, eds. Ausubel et al. (2000), which is herein incorporated by reference in its entirety for all purposes.) For example, denaturation temperatures under 94° C. select against amplification of fragments that are GC rich.

Competition between self-annealing and primer annealing can also be regulated by varying the length of the complementarity between the ends of the target sequence in relation to the length of complementarity between the target and the primer. Longer regions of complementarity, for example 30, 40 or 50 to 50, 80 or 100, base pairs between the ends of the fragment favor self-annealing and increased average length of the amplification product. Shorter regions of complementarity, for example 1, 5, 10 or 20 to 5, 10, or 25 base pairs of complementarity favors shorter amplification products. The complementary regions may be at the very ends of the fragments but may also be within 50 or 100 bases of the ends. Increased complementarity between the primer and the adaptor favors primer binding.

Inclusion of chain terminating nucleotides or nucleotide analogs can also be used to regulate the average length of an amplification product. Addition of a chain terminator such as ddATP, ddCTP, ddGTP, ddUTP and ddTTP results in the termination of extension whenever one of these is incorporated into an extending strand. The concentration of a chain terminator relative to its corresponding dNTP determines the frequency of termination. The result is that longer fragments are more likely to be prematurely terminated than shorter fragments. (See, Current Protocols in Molecular Biology, eds. Ausubel et al. (2000), which is herein incorporated by reference in its entirety for all purposes.) Useful concentrations of a chain terminator are, for example, dNTP:ddNTP equals 100:1 or 1000:1. The ratio of dNTP:ddNTP can be varied depending on the desired average length of the products and the relative binding affinities of the enzyme for the dNTP and ddNTP.

Inclusion of a 3' to 5' exonuclease activity favors amplification of long DNA by removing nucleotide misincorporations and preventing premature termination of strand synthesis. Conversely, absence of 3' to 5' exonuclease favors amplification of smaller fragments because of misincorporation of nucleotides leading to premature termination of strand synthesis. Many of the thermophilic DNA polymerases available for PCR are commercially available with or without 3' to 5' exonuclease activity, for example Vent and Vent (exo-) both available from New England Biolabs. Other components of the reaction can also be manipulated to effect the size of the amplification products by modifying polymerase fidelity. (See, for example, PCR Strategies, eds. Innis et al, Academic Press (1995), (Innis et al.),which is herein incorporated by reference for all purposes).

Shorter amplification products may also be selected by decreasing the extension and annealing times of the amplification reaction to, for example, from 2, 5, 10 or 20 to 5, 10 or 30 seconds, resulting in preferential amplification of shorter restriction fragments, because the likelihood of completing primer extension on longer fragments is less than on shorter fragments.

As those of skill in the art will appreciate, after amplification, the resulting sequences may be further analyzed using any known method including sequencing, HPLC, hybridization analysis, cloning, labeling, etc.

The materials for use in the present invention are ideally suited for the preparation of a kit suitable for obtaining a subset of a genome. Such a kit may comprise various reagents utilized in the methods, preferably in concentrated form. The reagents of this kit may comprise, but are not limited to, buffer, appropriate nucleotide triphosphates, appropriate dideoxynucleotide triphosphates, reverse transcriptases, nucleases, restriction enzymes, adaptors, ligases, DNA polymerases, terminal transferase, primers and instructions for the use of the kit.

(D.) Designing an Array to Interrogate Size Selected SNPs

In a particularly preferred embodiment the current invention is combined with in silico digestion techniques to predict the SNPs that will be present when a genome is digested with a particular enzyme or enzymes and a particular subset of fragments are amplified. In this embodiment a computer is first used to locate a SNP from the public database provided by The SNP Consortium (TSC), (available on the internet at snp.cshl.org last visited Jul. 25, 2001) in the public database of the sequence of the human genome, available in GenBank (See, ncbi.nlm.nih.gov, last visited Jul. 25, 2001). The computer is then used to predict the restriction sites for a particular enzyme upstream and downstream of a given SNP and to predict the resulting restriction fragment.

The SNPs and corresponding fragment sizes could be further separated by computer into subsets according to fragment size. In this way a computer could be used to identify all of the SNPs that are predicted to be found on fragments that are, for example, between 800 and 1600 base pairs in length when a sample DNA is digested with a given one or more restriction enzymes. In a preferred embodiment of the current invention splitting is used to reduce the size of these fragments to 400 to 800 base pairs prior to amplification. The information can also be used to design arrays to interrogate those SNPs predicted to be present in a particular size fraction resulting from a particular method of generating fragments to be amplified.

In Table 1, in silico digestion with different enzymes was used to predict restriction fragment lengths for the more than 800,000 SNPs in the TSC database and to identify those SNP containing fragments with lengths between 800 and 1500 base pairs. For example, when human genomic DNA is digested with PvuII 136,819 SNPs from the TSC database are predicted to be found on fragments that are between 800 and 1500 base pairs. This represents more than 20% of the SNPs in the TSC database. In one embodiment of the current invention several digests are combined to interrogate the desired number of SNPs. For example, in silico digestion predicts that combining the 800 to 1500 base pair fragments from digests using PvuII, NsiI and PstI should allow interrogation of approximately 40% of the SNPs in the database.

TABLE 1

Prediction of SNP containing fragments with lengths between 800 and 1500 base pairs by in silico digestion.

| Restriction Enzyme | SNPs on Fragments | SNPs on Fragments of 800–1500 bp | Percent of SNPs on 809–1500 bp fragments |
|---|---|---|---|
| PvuII | 653501 | 136819 | 20.9 |
| NsiI | 649122 | 79229 | 12.2 |
| PstI | 659081 | 70850 | 10.7 |
| HindIII | 635752 | 41738 | 6.6 |
| BsrGI | 626285 | 36246 | 5.8 |
| XbaI | 631415 | 35506 | 5.6 |
| BglII | 627495 | 34561 | 5.5 |
| EcoRI | 632078 | 34244 | 5.4 |
| NcoI | 610472 | 33846 | 5.5 |
| BclI | 616261 | 31175 | 5.1 |
| SacI | 579210 | 23725 | 4.1 |
| ApaI | 524802 | 17423 | 3.3 |
| BamHI | 535953 | 16294 | 3.0 |
| ApaLI | 556948 | 14680 | 2.6 |
| KpnI | 505444 | 4867 | 1.0 |
| XhoI | 516532 | 1155 | 0.2 |
| BspEI | 547247 | 901 | 0.2 |
| SalI | 683138 | 101 | 0.0 |

The current invention further provides methods to combine in silico prediction of the size of SNP containing fragments with methods of splitting and size selection by PCR to design genotyping assays and arrays for genotyping. In this embodiment of the current invention an array is designed to interrogate the SNPs that are predicted to be found in a size fraction resulting from digestion of the first nucleic acid sample with one or more particular restriction enzymes followed by splitting. For example, a computer may be used to search the sequence of a genome to identify all recognition sites for the restriction enzyme, EcoRI. The computer can then be used to predict the size of all restriction fragments resulting from an EcoRI digestion and to identify those fragments that contain a known or suspected SNP. The computer may then be used to identify the group of SNPs that are predicted to be found on fragments of, for example, 400–1600 base pairs, when genomic DNA is digested with EcoRI. An array may then be designed to interrogate that subset of SNPs that are found on EcoRI fragments of 400–1600 base pairs.

One set of PCR conditions can be used to obtain SNP information about two different size ranges of fragments. For example, PCR conditions that are optimized to amplify fragments of 400–800 base pairs can be used to analyze SNPs in fragments that are in both the 400 to 800 base pair range and the 800 to 1600 base pair range.

The design of the array may be further refined by adding additional information about each SNP. For example, subsequently obtained empirical data about a particular SNP may indicate that fewer probes are necessary to determine the presence of a given allele. SNPs that prove to be of particular biological importance may be added and SNPs that are subsequently shown to be of little or no biological importance can be removed.

Arrays will preferably be designed to interrogate 100, 500, 1000, 5000, 10,000, 50,000 or 100,000 different SNPs. For example, an array may be designed to recognize a group of SNPs predicted to be present on 400–1600 base pair EcoRI fragments, 400–1600 BglII fragments, 400–1600 XbaI fragments, and 400–1600 HindIII fragments. One or more PCR products, that differ in the restriction enzyme used for fragmentation or the conditions of amplification, could be pooled prior to hybridization to increase the complexity of the sample.

In one embodiment of the invention a single size selected amplification product is suitable for hybridization to many different arrays. For example, a single method of fragmentation and amplification that is suitable for hybridization to an array designed to interrogate SNPs contained on 400–800 base pair EcoRI would also be suitable for hybridization to an array designed to interrogate SNPs contained on 400–800 base pair BamHI fragments. This would introduce consistency and reproducibility to sample preparation methods.

Methods of Use

The methods of the presently claimed invention can be used for a wide variety of applications. Any analysis of genomic DNA may be benefited by a reproducible method of complexity management. Furthermore, the methods and enriched fragments of the presently claimed invention are particularly well suited for study and characterization of extremely large regions of genomic DNA.

In a preferred embodiment, the methods of the presently claimed invention are used for SNP discovery and to genotype individuals. For example, any of the procedures described above, alone or in combination, could be used to isolate the SNPs present in one or more specific regions of genomic DNA. Selection probes could be designed and manufactured to be used in combination with the methods of the invention to amplify only those fragments containing regions of interest, for example a region known to contain a SNP. Arrays could be designed and manufactured on a large scale basis to interrogate only those fragments containing the regions of interest. Thereafter, a sample from one or more individuals would be obtained and prepared using the same techniques which were used to prepare the selection probes or to design the array. Each sample can then be hybridized to an array and the hybridization pattern can be analyzed to determine the genotype of each individual or a population of individuals. Methods of use for polymorphisms and SNP discovery can be found in, for example, co-pending U.S. application Ser. Nos. 08/813,159 and 09/428,350 which are herein incorporated by reference in their entirety for all purposes).

Correlation of Polymorphisms with Phenotypic Traits

Most human sequence variation is attributable to or correlated with SNPs, with the rest attributable to insertions or deletions of one or more bases, repeat length polymorphisms and rearrangements. On average, SNPs occur every 1,000–2,000 bases when two human chromosomes are compared. (See, The International SNP Map Working Group, Science 409: 928–933 (2001) incorporated herein by reference in its entirety for all purposes.) Human diversity is limited not only by the number of SNPs occurring in the genome but further by the observation that specific combinations of alleles are found at closely linked sites.

Correlation of individual polymorphisms or groups of polymorphisms with phenotypic characteristics is a valuable tool in the effort to identify DNA variation that contributes to population variation in phenotypic traits. Phenotypic traits include physical characteristics, risk for disease, and response to the environment. Polymorphisms that correlate with disease are particularly interesting because they represent mechanisms to accurately diagnose disease and targets for drug treatment. Hundreds of human diseases have already been correlated with individual polymorphisms but there are many diseases that are known to have an, as yet unidentified, genetic component and many diseases for which a component is or may be genetic.

Many diseases may correlate with multiple genetic changes making identification of the polymorphisms associated with a given disease more difficult. One approach to overcome this difficulty is to systematically explore the limited set of common gene variants for association with disease.

To identify correlation between one or more alleles and one or more phenotypic traits, individuals are tested for the presence or absence of polymorphic markers or marker sets and for the phenotypic trait or traits of interest. The presence or absence of a set of polymorphisms is compared for individuals who exhibit a particular trait and individuals who exhibit lack of the particular trait to determine if the presence or absence of a particular allele is associated with the trait of interest. For example, it might be found that the presence of allele A1 at polymorphism A correlates with heart disease. As an example of a correlation between a phenotypic trait and more than one polymorphism, it might be found that allele A1 at polymorphism A and allele B1 at polymorphism B correlate with a phenotypic trait of interest.

Diagnosis of Disease and Predisposition to Disease

Markers or groups of markers that correlate with the symptoms or occurrence of disease can be used to diagnose disease or predisposition to disease without regard to phenotypic manifestation. To diagnose disease or predisposition to disease, individuals are tested for the presence or absence of polymorphic markers or marker sets that correlate with one or more diseases. If, for example, the presence of allele A1 at polymorphism A correlates with coronary artery disease then individuals with allele A1 at polymorphism A may be at an increased risk for the condition.

Individuals can be tested before symptoms of the disease develop. Infants, for example, can be tested for genetic diseases such as phenylketonuria at birth. Individuals of any age could be tested to determine risk profiles for the occurrence of future disease. Often early diagnosis can lead to more effective treatment and prevention of disease through dietary, behavior or pharmaceutical interventions. Individuals can also be tested to determine carrier status for genetic disorders. Potential parents can use this information to make family planning decisions.

Individuals who develop symptoms of disease that are consistent with more than one diagnosis can be tested to make a more accurate diagnosis. If, for example, symptom S is consistent with diseases X, Y or Z but allele A1 at polymorphism A correlates with disease X but not with diseases Y or Z an individual with symptom S is tested for the presence or absence of allele A1 at polymorphism A. Presence of allele A1 at polymorphism A is consistent with a diagnosis of disease X. Genetic expression information discovered through the use of arrays has been used to determine the specific type of cancer a particular patient has. (See, Golub et al. Science 286: 531–537 (2001) hereby incorporated by reference in its entirety for all purposes.)

Pharmacogenomics

Pharmacogenomics refers to the study of how genes affect response to drugs. There is great heterogeneity in the way individuals respond to medications, in terms of both host toxicity and treatment efficacy. There are many causes of this variability, including: severity of the disease being treated; drug interactions; and the individuals age and nutritional status. Despite the importance of these clinical variables, inherited differences in the form of genetic polymorphisms can have an even greater influence on the efficacy and toxicity of medications. Genetic polymorphisms in drug-metabolizing enzymes, transporters, receptors, and other drug targets have been linked to interindividual differences in the efficacy and toxicity of many medications. (See, Evans and Relling, Science 286: 487–491 (2001) which is herein incorporated by reference for all purposes).

An individual patient has an inherited ability to metabolize, eliminate and respond to specific drugs. Correlation of polymorphisms with pharmacogenomic traits identifies those polymorphisms that impact drug toxicity and treatment efficacy. This information can be used by doctors to determine what course of medicine is best for a particular patient and by pharmaceutical companies to develop new drugs that target a particular disease or particular individuals within the population, while decreasing the likelihood of adverse affects. Drugs can be targeted to groups of individuals who carry a specific allele or group of alleles. For example, individuals who carry allele A1 at polymorphism A may respond best to medication X while individuals who carry allele A2 respond best to medication Y. A trait may be the result of a single polymorphism but will often be determined by the interplay of several genes.

In addition some drugs that are highly effective for a large percentage of the population, prove dangerous or even lethal for a very small percentage of the population. These drugs typically are not available to anyone. Pharmacogenomics can be used to correlate a specific genotype with an adverse drug response. If pharmaceutical companies and physicians can accurately identify those patients who would suffer adverse responses to a particular drug, the drug can be made available on a limited basis to those who would benefit from the drug.

Similarly, some medications may be highly effective for only a very small percentage of the population while proving only slightly effective or even ineffective to a large percentage of patients. Pharmacogenomics allows pharmaceutical companies to predict which patients would be the ideal candidate for a particular drug, thereby dramatically reducing failure rates and providing greater incentive to companies to continue to conduct research into those drugs.

Determination of Relatedness

There are many circumstances where relatedness between individuals is the subject of genotype analysis and the present invention can be applied to these procedures. Paternity testing is commonly used to establish a biological relationship between a child and the putative father of that child. Genetic material from the child can be analyzed for occurrence of polymorphisms and compared to a similar analysis of the putative father's genetic material. Determination of relatedness is not limited to the relationship between father and child but can also be done to determine the relatedness between mother and child, (see e.g. Staub et al., U.S. Pat. No. 6,187,540) or more broadly, to determine how related one individual is to another, for example, between races or species or between individuals from geographically separated populations, (see for example H. Kaessmann, et al. *Nature Genet.* 22, 78 (1999)).

Forensics

The capacity to identify a distinguishing or unique set of forensic markers in an individual is useful for forensic analysis. For example, one can determine whether a blood sample from a suspect matches a blood or other tissue sample from a crime scene by determining whether the set of polymorphic forms occupying selected polymorphic sites is the same in the suspect and the sample. If the set of polymorphic markers does not match between a suspect and a sample, it can be concluded (barring experimental error) that the suspect was not the source of the sample. If the set of markers does match, one can conclude that the DNA from the suspect is consistent with that found at the crime scene. If frequencies of the polymorphic forms at the loci tested have been determined (e.g., by analysis of a suitable population of individuals), one can perform a statistical analysis to determine the probability that a match of suspect and crime scene sample would occur by chance. A similar comparison of markers can be used to identify an individual's remains. For example the U.S. armed forces collect and archive a tissue sample for each service member. If unidentified human remains are suspected to be those of an individual a sample from the remains can be analyzed for markers and compared to the markers present in the tissue sample initially collected from that individual.

Marker Assisted Breeding

Genetic markers can assist breeders in the understanding, selecting and managing of the genetic complexity of animals and plants. Agriculture industry, for example, has a great deal of incentive to try to produce crops with desirable traits (high yield, disease resistance, taste, smell, color, texture, etc.) as consumer demand increases and expectations change. However, many traits, even when the molecular mechanisms are known, are too difficult or costly to monitor during production. Readily detectable polymorphisms which are in close physical proximity to the desired genes can be used as a proxy to determine whether the desired trait is present or not in a particular organism. This provides for an efficient screening tool which can accelerate the selective breeding process.

EXAMPLES

Example 1

Splitting and PCR Amplification of Split Fragments

Figure 2:
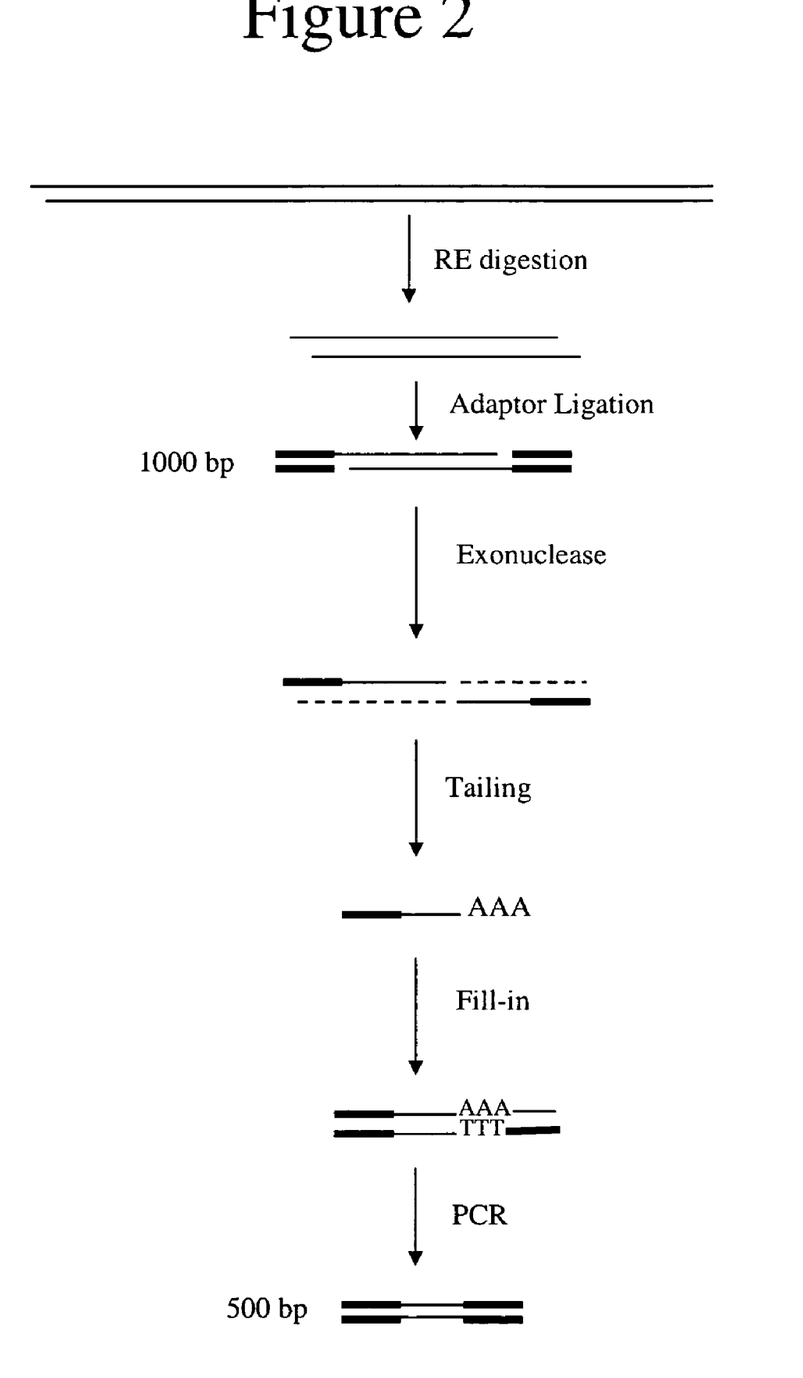
FIG. 2 shows a schematic of size selection using exonuclease digestion.

FIG. 2 shows a schematic representation of fragment selection by PCR after splitting with an exonuclease.

Target Preparation

10 μl of 0.1 μg/μl human genomic DNA can be digested in a 40 μl reaction volume with 20 units restriction enzyme PvuII, in 1× RE buffer (NEB) and 1 μg/μl BSA for 2 hours at 37° C.

To convert the blunt ends created by digestion with PvuII to two base sticky ends the digested DNA can be mixed with 4 ul of 2.5 mM each dCTP and dTTP, 5 units Klenow in a 45 ul reaction at 37° C. for 20 min. The enzyme can be heat-inactivated at 75° C. for 20 min.

The DNA can then be purified with a Qiagen PCR clean-up kit and eluted in 40 ul elution buffer.

Adaptors are then ligated to the DNA by mixing 40 ul DNA with 1 ul of a 25 uM solution of adaptor, 5'AGTATAAGGCGTTCGTCA3' (SEQ ID NO: 1) and 5'pAGTGACGAACGCCTTATACT3' (SEQ ID NO: 2) and 1000 units of ligase in 50 ul ligase buffer. The reaction is incubated at 16° for 2 hours to overnight. The DNA can then be purified with a Qiagen PCR clean up kit and eluted in 40 ul elution buffer.

Fragment Splitting

The DNA is then digested with Exo III. 20 ul of the ligated DNA can be mixed with 0.5 ul 25 mM MgCl2, 1 ul 2 ug/ul T4Gene32, 100 units ExoIII and 2.5 ul 10× buffer (1 mg/ml BSA, 500 mM TrisHCL pH 8) in a 25 ul final reaction volume. This is then incubated at 37° C. for 30 min followed by 95° C. for 10 min.

Tailing

The 25 ul digest is mixed with 6 ul 5×TdT buffer (Promega), 1.5 ul 2 mM dATP, 0.05 mM ddTTP, and 0.5 ul 20 units/ul TdT and incubated at 37° C. for 30 min followed by 95° C. for 10 min.

Fill-in

The 33 ul tailing reaction is then mixed with 10 ul 10× polymerase buffer (NEB), 10 ul 2.5 mM dNTPs, 5 ul 10 uM primer, 5'AGTATAAGGCGTTCGTCACTG TCATTTTTTTTTTTTTTTTTT3' (SEQ ID NO: 3) in a final reaction volume of 100 ul. This is incubated at 95° C. for 1 min to denature the DNA and then cooled to 4° C. 1 ul Klenow, 5 units/ul is added and the reaction is incubated at 25° C. for 25 min followed by 37° C. for 15 min and finally 95° C. for 10 min.

Amplification

PCR is done in a 100 ul reaction with 10 ul 10× buffer II, 8 ul 25 mM MgCl2, 10 ul 2.5 mM dNTPs, 5 ul 10 uM primer, 5'AGTATAAGGCGTTCGTCACTG3' (SEQ ID NO: 4), 1 ul 5 units/ul TaqGold (Perkin Elmer) and 5 ul DNA. The reaction is first incubated at 95° C. for 10 min then 40 cycles of 95° C. for 20 sec, 55° C. for 20 sec and 72° C. for 20 sec.

Fragmentation, labeling and hybridization can be done using standard procedures.

CONCLUSION

From the foregoing it can be seen that the present invention provides a flexible and scalable method for analyzing complex samples of DNA, such as genomic DNA. These methods are not limited to any particular type of nucleic acid sample: plant, bacterial, animal (including human) total genome DNA, RNA, cDNA and the like may be analyzed using some or all of the methods disclosed in this invention. This invention provides a powerful tool for analysis of complex nucleic acid samples. From experiment design to isolation of desired fragments and hybridization to an appropriate array, the above invention provides for fast, efficient and inexpensive methods of complex nucleic acid analysis.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

I claim:

1. A method for analyzing a first nucleic acid sample comprising:
    obtaining a second nucleic acid sample by:
        fragmenting the first nucleic acid sample to produce double stranded fragments;
        ligating one or more adaptors to the double stranded fragments;
        digesting the adaptor ligated double stranded fragments to produce single stranded half molecules;
        adding a homopolymeric tail to the 3' end of the single stranded half molecules, hybridizing a primer to the homopolymeric tail and extending the primer to generate double stranded half fragments from the single stranded half molecules; and
        amplifying a plurality of the double stranded half fragments by a polymerase chain reaction (PCR) wherein the size of the amplified fragments is modulated by varying one or more reaction conditions or reagents to reduce the complexity of the first nucleic acid sample;
    providing a nucleic acid array;
    hybridizing the second nucleic acid sample to the array; and
    analyzing a hybridization pattern resulting from the hybridization.

2. The method of claim 1 wherein the reaction condition or reagent varied is chosen from the group consisting of: extension time, annealing time, primer concentration, primer length, presence or absence of 3' to 5' exonuclease activity, and concentration of nucleotide analogues.

3. The method of claim 1 wherein the method for analyzing a first nucleic acid sample comprises determining whether the first nucleic acid sample contains sequence variations.

4. The method of claim 3 wherein the sequence variations are single nucleotide polymorphisms (SNPs).

5. The method of claim 1 wherein the nucleic acid array is designed to query DNA fragments which have been produced by the procedures used to obtain the second nucleic acid sample.

6. The method of claim 1 wherein a substantial amount of the sequences predicted to be contained in the second nucleic acid sample are predetermined.

7. The method of claim 1 wherein a substantial amount of the sequences predicted to be contained in the second nucleic acid sample are first determined by a computer system.

8. A method of screening for DNA sequence variations in an individual comprising:
   providing a first nucleic acid sample from the individual;
   obtaining a second nucleic acid sample by:
      fragmenting the first nucleic acid sample to produce double stranded fragments;
      ligating adaptor sequences to the double stranded fragments;
      digesting the adaptor ligated double stranded fragments to produce single stranded half molecules;
      adding a homopolymeric tail to the 3' end of the single stranded half molecules, hybridizing a primer to the homopolymeric tail and extending the primer to generate double stranded half fragments from the single stranded half molecules; and,
      amplifying a subset of the double stranded half fragments by a polymerase chain reaction (PCR) wherein one or more reaction conditions or reagents are varied to favor amplification of a subset of fragments of a specific size range;
   providing a nucleic acid array wherein the array comprises probes designed to interrogate for DNA sequence variations;
   hybridizing the second nucleic acid sample to the array;
   generating a hybridization pattern resulting from the hybridization; and
   determining the presence or absence of DNA sequence variations in the individual based upon an analysis of the hybridization pattern.

9. The method of claim 8 wherein the sequence variation is a single nucleotide polymorphism (SNP).

10. The method of claim 8 wherein the SNP is associated with a disease.

11. The method of claim 8 wherein the SNP is associated with the efficacy of a drug.

12. A method for screening for DNA sequence variations in a population of individuals comprising:
   providing a first nucleic acid sample from each of the individuals;
   providing a second nucleic acid sample by:
      fragmenting the first nucleic acid sample to produce double stranded fragments;
      ligating adaptor sequences to the double stranded fragments;
      digesting the adaptor ligated double stranded fragments to produce single stranded half molecules;
      adding a homopolymeric tail to the 3' end of the single stranded half molecules, hybridizing a primer to the homopolymeric tail and extending the primer to generate double stranded half fragments from the single stranded half molecules;
      amplifying a subset of the double stranded half fragments by a polymerase chain reaction (PCR) wherein one or more reaction conditions or reagents are varied to favor amplification of a subset of fragments of a specific size range; and
   providing a plurality of nucleic acid arrays wherein the arrays comprise probes designed to interrogate for DNA sequence variations;
   hybridizing each of the second nucleic acid samples to one of the plurality of arrays;
   generating a plurality of hybridization patterns resulting from the hybridizations; and
   analyzing the hybridization patterns to determine the presence or absence of sequence variation in the population of individuals.

13. The method of claim 12 wherein the sequence variation is a single nucleotide polymorphism (SNP).

14. The method of claim 12 further comprising the steps of diluting the product of the PCR and amplifying the diluted product by a second round of PCR.

15. A method of genotyping an individual comprising:
   identifying a collection of SNPs that are found on fragments of a selected size range resulting from digestion with one or more selected restriction enzymes;
   designing an array to interrogate the collection of SNPs;
   providing a first nucleic acid sample from the individual;
   fragmenting the first nucleic acid sample with the one or more selected restriction enzymes to produce double stranded fragments;
   ligating adaptor sequences to the double stranded fragments;
   digesting the adaptor ligated double stranded fragments to produce single stranded half molecules;
   adding a homopolymeric tail to the 3' end of the single stranded half molecules, hybridizing a primer to the homopolymeric tail and extending the primer to generate double stranded half fragments from the single stranded half molecules;
   amplifying the double stranded half fragments by PCR wherein a subset of fragments of the selected size range are preferentially amplified to obtain a PCR product;
   hybridizing the PCR product to an array; and
   analyzing the hybridization pattern to determine the presence or absence of the collection of SNPs.

* * * * *

SEQUENCE LISTING

```
<160> NUMBER OF SEQ ID NOS: 4

<210> SEQ ID NO 1
<211> LENGTH: 18
<212> TYPE: DNA
<213> ORGANISM: artificial sequence
<220> FEATURE:
<223> OTHER INFORMATION: synthetic oligonucleotide

<400> SEQUENCE: 1
agtataaggc gttcgtca                                               18

<210> SEQ ID NO 2
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 2
agtgacgaac gccttatact                                             20

<210> SEQ ID NO 3
<211> LENGTH: 41
<212> TYPE: DNA
<213> ORGANISM: artificial sequence
<220> FEATURE:
<223> OTHER INFORMATION: synthetic oligonucleotide

<400> SEQUENCE: 3
agtataaggc gttcgtcact gtcatttttt tttttttttt t                     41

<210> SEQ ID NO 4
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 4
agtataaggc gttcgtcact g                                           21
```